United States Patent [19]

Hawkins

[11] 4,271,002
[45] Jun. 2, 1981

[54] CALCIUM ION-SELECTIVE ELECTRODES AND MEMBRANE FOR USE THEREIN

[75] Inventor: John J. Hawkins, Santa Ana, Calif.

[73] Assignee: Beckman Instruments, Inc., Fullerton, Calif.

[21] Appl. No.: 107,031

[22] Filed: Dec. 26, 1979

Related U.S. Application Data

[63] Continuation-in-part of Ser. No. 52,639, Jun. 27, 1979, which is a continuation-in-part of Ser. No. 880,908, Feb. 24, 1978, abandoned.

[51] Int. Cl.$^3$ .......................................... G01N 27/46
[52] U.S. Cl. .............................. 204/195 M; 204/1 T; 204/1 A; 544/110
[58] Field of Search ................... 204/1 T, 1 A, 195 M

[56] References Cited

U.S. PATENT DOCUMENTS

| | | | |
|---|---|---|---|
| 3,429,785 | 2/1969 | Ross | 204/195 L |
| 3,438,886 | 4/1969 | Ross | 204/195 L |
| 3,445,365 | 5/1969 | Ross | 204/195 L |
| 3,448,032 | 6/1969 | Settzo et al. | 204/195 L |
| 3,691,047 | 9/1972 | Ross et al. | 204/195 M |
| 3,729,401 | 4/1973 | Cosgrove et al. | 204/195 L |
| 3,856,649 | 12/1974 | Genshaw | 204/195 M |
| 3,932,233 | 1/1976 | Ruzicka et al. | 204/195 M |

OTHER PUBLICATIONS

Steward et al., "J. Am. Chem. Soc.," 73:1377–1379, (1951).
Schwartz, "Clin. Chem.", 22, (4):461–467, (1976).
Hulamicki et al., "Analytica Chimica Acta," 87:411–417, (1976).
Owen et al., "Analytica Chimica Acta", 90:241–244, (1977).
Fuchs et al., "Clin. Chem.", 23, (3):610, (1977).
Cattrall et al., "Analytica Chimica Acta", 76:269–277, (1975).
Schwartz, "Clinica Chimica Acta", 64:227–239, (1975).
Ammann et al., "Analytical Letters", 8, (10):709–720, (1975).
Fuchs et al., "Clinica Chimica Acta", 67:99–102, (1976).
Ruzicka et al., "Analytica Chimica Acta", 67:155–178, (1973).
Morf et al., "Analytical Letters", 7, (1):9–22, (1974).
Thomas, "Proc. Soc. Analyt. Chem.", 340–342, (Dec. 1974).
Pretsch et al., "Research Development", 20–24, (Mar. 1974).
Moody et al., "Analyst", 95:910–918, (1970).
Cattrall et al., "Analytical Chemistry", 43, (13):1905–1906, (1971).
Griffiths et al., "Analyst", 97:420–427, (1972).
Subryan et al., "Clinical Chemistry", 18, (12):1459–1462, (1972).
Koryta, "Analytica Chimica Acta", 61:329–411, (1972).
Buck, "Analytical Chemistry", 46, (5):28R–51R, (1974).
Koryta, "Analytica Chimica Acta", 91:1–85, (1977).
Buck, "Analytical Chemistry", 50, (5):17R–29R, (1978).
Craggs et al., "Analyst," 104:412–418, (1979).
Partridge et al., "J. Inorg. Nucl. Chem.", 31:2587–2589, (1969).
Griffiths et al., "J. Inorg. Nucl. Chem.", 34:3043–3048, (1972).
Moody et al., "Analyst," 103:68–71, (1978).

*Primary Examiner*—T. Tung
*Attorney, Agent, or Firm*—R. J. Steinmeyer; Robert R. Meads; Robert S. Frieman

[57] ABSTRACT

A membrane for use in the determination of calcium ion concentration in an aqueous solution, the membrane being of the type comprising a calcium ion selective component and a carrier material. The membrane is characterized in that the calcium ion selective component is a compound having a formula (I)

$$\begin{array}{c} X-O \quad O \\ \quad \diagdown \| \\ Y-O-P-O^{-+}H \quad Z \\ \diagdown \diagup \\ N \\ \diagup \diagdown \\ \Big( \quad \Big) \\ \diagdown \diagup \\ O \end{array} \quad (I)$$

wherein
X and Y are independently selected from the group consisting of aryl, alkyl(aryl), alkenyl(aryl), alkynyl(aryl), alkyl, cycloalkyl, alkenyl, cycloalkenyl, and alkynyl radicals wherein said alkyl moiety of said alkyl(aryl) radical consists of 1-12 carbon atoms; each alkenyl and alkynyl moiety of said alkenyl(aryl) and alkynyl(aryl) radicals, respectively, consists of 2-12 carbon atoms; each aryl moiety consists of 6, 10, 12, or 14 carbon atoms; and each alkyl, cycloalkyl, alkenyl, cycloalkenyl, and alkynyl radical consists of 6 to 14 carbon atoms; and Z is selected from a group consisting of alkyl radicals containing 1-12 carbon atoms; alkenyl and alkynyl radicals containing 4-12 carbon atoms; and cycloalkyl and cycloalkenyl radicals containing 6 to 12 carbom atoms.

The membrane can be employed in an electrode system.

A novel compound of formula I, supra, and a method for the manufacture thereof.

75 Claims, 6 Drawing Figures

PRIOR ART ELECTRODE
(EXAMPLE 10)

FIG. 6

ELECTRODE WITHIN SCOPE OF INVENTION
(EXAMPLE 8)

CALCIUM ION-SELECTIVE ELECTRODES AND MEMBRANE FOR USE THEREIN

CROSS-REFERENCE TO RELATED APPLICATIONS

This application is a continuation in part of application Ser. No. 052,639, filed June 27, 1979, which is a continuation-in-part of application Ser. No. 880,908, filed Feb. 24, 1978, now abandoned.

BACKGROUND OF THE INVENTION

1. Field of the Invention

This invention relates to a calcium ion-selective electrode and to a calcium ion-selective membrane for use therein.

2. Description of the Prior Art

Extensive research has been undertaken in the area of calcium ion-selective electrodes as evidenced by the extensive patent (5-10) and technical (11-30) literature in this area and the development and state of the art with respect to these electrodes has been documented (1-4).

More specifically, U.S. Pat. No. 3,729,401 (8) discloses the use of the diester of t-octylphenyl phosphoric acid as the calcium ion selector dissolved in an organic liquid such as di-n-octylphenylphosphonate. U.S. Pat. No. 3,932,233 (10) is directed to the calcium salts of di-(aryl)phosphates and di(n-alkylaryl) phosphates in admixture with their respective acid phosphates and combined with polyvinyl chloride and di-n-octyl phenylphosphonate. Griffiths et al. (13) formed a solid membrane system using polyvinyl chloride. Griffiths et al. (13) found that there was an optimum mixture in formulating the calcium membrane when monocalcium dihydrogen tetra(didecylphosphate) was used in a weight ratio of 1:10 with di-n-octyl phenylphosphonate plasticizer. This latter mixture was used in 71.2% concentrations by weight with 28.8% polyvinyl chloride homopolymer added. The calcium acid tetra salt of the diester phosphate was made up by mixing equal portions of the diester acid phosphate with monocalcium di(didecylphosphate). The work of Griffiths et al. (13) was classic in calcium ion electrode technology and has been copied by many workers in the art. Thus, it is considered necessary by those skilled in the art to incorporate the ion sensing phosphate ligand as a calcium acid salt form into the plasticized membrane. Hence, all purifications of the diester phosphates have involved the isolation of both the diester acid phosphate and the calcium salt diester phosphate and then combining the two equivalent ingredients into the phosphonate plasticizer in the 1:10 ratio.

Recently, Moody et al. (30) have disclosed that one can obtain satisfactory results using just the calcium salt of bis[di(p-1,1,2,2-tetramethylbutylphenyl) phosphate] in conjunction with a plasticizer in a ratio of up to 1 part calcium salt to 10 parts plasticizer.

However, serious shortcomings exist with the prior art calcium electrodes. These shortcomings include (1) a relatively slow response of the calcium electrode; (2) a relatively poor selectivity to calcium in the lower ion concentration ranges; (3) a relatively poor use life; and (4) a relatively difficult manufacturing process entailed in the manufacture thereof.

It would therefore be very advantageous to have a calcium electrode and membrane for use therein which overcomes these problems present in the prior art.

SUMMARY OF THE INVENTION

In accordance with the present invention there are provided a calcium ion electrode and a calcium ion-selective membrane for use therein which possesses (1) a fast response to calcium ion concentrations, (2) an excellent selectivity to calcium in the lower ion concentration ranges; (3) an extended use life; and (4) a simplified manufacturing process in the production thereof.

More particularly, the membrane for use in the determination of calcium ion concentration is of the type comprising a calcium ion-selective component and a carrier material. The membrane is characterized in that the calcium ion-selective component is a compound having a formula I wherein X and Y are independently selected from a group consisting of aryl, alkyl(aryl), alkenyl(aryl), alkynyl(aryl), alkyl, cycloalkyl, alkenyl, cycloalkenyl and alkynyl radicals. The alkyl moiety of the alkyl(aryl) radical consists of 1-12 carbon atoms. Each alkenyl and alkynyl moiety of the alkenyl(aryl) and alkynyl(aryl) radicals, respectively, consist of 2-12 carbon atoms. Each aryl moiety consists of 6, 10, 12, or 14 carbon atoms; and each alkyl, cycloalkyl, alkenyl, cycloalkenyl, and alkynyl radical consists of 6-14 carbon atoms. Z is selected from a group consisting of alkyl radicals containing 1-12 carbon atoms; alkenyl and alkynyl radicals containing 4-12 carbon atoms; and cycloalkyl and cycloalkenyl radicals containing 6-12 carbon atoms.

The improved electrode of the instant invention is of the type comprising a membrane and means, including an electrode substrate, for supporting the membrane. The improved electrode is characterized in that the above described membrane is employed therein.

Also encompassed with the scope of the present invention is the compound of formula I, supra, and a method for the manufacture thereof.

DESCRIPTION OF THE PREFERRED EMBODIMENTS

The membrane of the instant invention employed for use in the determination of calcium ion concentration is of the type comprising a calcium ion-selecting component and a carrier material. The membrane is characterized in that the calcium ion-selective component is a compound having a formula I wherein X and Y are selected from a group consisting of aryl, alkyl(aryl), alkenyl(aryl), alkynyl(aryl), alkyl, cycloalkyl, alkenyl, cycloalkenyl, and alkynyl radicals. The alkyl moiety of the alkyl(aryl) radical consists of 1–12 carbon atoms. Each alkenyl and alkynyl moiety of the alkenyl(aryl) and alkynyl(aryl) radicals, respectively, consists of 2–12 carbon atoms. Each aryl moeity consists of 6, 10, 12, or 14 carbon atoms. Each alkyl, cycloalkyl, alkenyl, cycloalkenyl, and alkynyl radical consists of 6–14 carbon atoms. Z is selected from a group consisting of alkyl radicals containing 1–12 carbon atoms; alkenyl and alkynyl radicals containing 4–12 carbon atoms; and cycloalkyl and cycloalkenyl radicals containing 6–12 carbon atoms.

Preferably X and Y are the same.

Examples of akyl(aryl), alkenyl(aryl), and alkynyl(aryl) radicals which can be employed in the instant invention include, but are not limited to, (t-butyl)phenyl, p-(t-butyl)diphenyl, (t-butyl)naphthyl, (n-octyl)phenyl, (iso-octyl)phenyl, (t-octyl)phenyl, (t-octyl)napthyl, (methyl)phenyl, (ethyl)phenyl, (n-propyl)phenyl, (iso-propyl)phenyl, (n-butyl)phenyl, (iso-butyl)phenyl, (n-pentyl)phenyl, (n-hexyl)phenyl, (1,2-dimethylbutyl)phenyl, (2-ethylhexyl)phenyl, (iso-nonyl)phenyl, (n-decyl)phenyl, (iso-decyl)phenyl, and (n-dodecyl)phenyl. Alkyl(aryl) radicals which are derivatives of commercially available compounds include p-(1,1,3,3-tetramethylbutyl)phenyl, p-(iso-decyl)phenyl, p-(n-decyl)phenyl, p-(2-ethylhexyl)phenyl and p-(n-octyl)phenyl.

Examples of alkyl, cycloalkyl, alkenyl, cycloalkenyl, and alkynyl radicals which can be employed in the instant invention include, but are not limited to, cyclohexyl, cyclooctyl, cyclooctenyl, octenyl-1, cyclododecyl, dodecentyl-1, t-butyl, 3-butynyl, n-octyl, iso-octyl, t-octyl, methyl, ethyl, n-propyl, isopropyl, n-butyl, isobutyl, n-pentyl, n-hexyl, 1-heptynyl, 1,2-dimethylbutyl, 2-ethylhexyl, iso-nonyl, n-decyl, iso-decyl, and n-dodecyl. Preferred alkyl radicals include n-octyl, isononyl, n-dodecyl, n-decyl, and iso-decyl.

Examples of alkyl, alkenyl, alkynyl, cycloalkyl, and cycloalkenyl radicals which can be employed as Z in the instant invention include, but are not limited to, cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl. Preferably, Z is ethyl.

The calcium ion-selective component of formula I can be synthesized via the following procedure. First, a compound having a formula II wherein X and Y are as defined above, is either prepared via any well known procedure, e.g., that exemplified in U.S. Pat. No. 3,932,233, or purchased from a chemical supplier. The compound of formula II, whether made or purchased, is usually present in a a mixture containing the desired compound II and at least one reaction co-product selected from a group consisting of and wherein X and Y are as defined above and wherein E is selected from the same group from which X and Y are selected. Compound II can be separated from the above mixture via a separation procedure which entails:
(a) mixing the mixture with a solvent selected from a group consisting of heptane, cyclohexane, and mixtures thereof;
(b) mixing ethylene glycol with the product of step (a);
(c) allowing the mixture of step (b) to form a hydrocarbon layer and an ethylene glycol layer;
(d) separating the hydrocarbon layer from the ethylene glycol layer; and
(e) extracting the hydrocarbon layer at least once with water.

To the extracted hydrocarbon layer of step (e) is then added (as step f) a compound having the formula VI wherein Z is as defined above, thereby forming the compound of formula I.

This process can be done at any convenient temperature and is preferably conducted at room temperature. Preferably, steps (b), (c), and (d) are repeated 3 or more times and step (e) is repeated 2 or more times. Furthermore, to avoid the formation of colloids during the water extraction step (e), slightly acidic water (i.e., water having a pH below 5.5, preferably from about 3 to about 5, and more preferably from about 4 to about 5) is desirable for use in step (e). It is also preferred that after step (e) and prior to step (f) the extracted hydrocarbon layer be contacted with a suitable neutral anhydrous dessicant, e.g., anhydrous sodium sulfate. The dessicant can be removed from the hydrocarbon layer via any convenient separation process, e.g., filtration, to thereby obtain a dried hydrocarbon layer for use in step (f).

In the broadest sense of the instant invention, the carrier material employed in the membrane of the instant invention can be formulated from any material which has been employed as a carrier material by those skilled in the art. In one preferred embodiment of the instant invention, the carrier material employed in the membrane comprises a first lipophilic-hydrophobic (LH) layer and a second LH layer in intimate contact with the first layer, the calcium ion-selective component being present in the second layer. The first LH layer can comprise an adhesive, LH polymer having an intrinsic viscosity of from about 0.4 to about 0.9, preferably from about 0.5 to about 0.7, and more preferably about 0.6, ml/g; and a LH plasticizer. The adhesive, LH polymer is preferably selected from a group consisting of halogenated and unhalogenated aliphatic, cycloaliphatic, and aromatic polymers, copolymers, and terpolymers, as well as block polymers and graph polymers thereof. More preferably, the adhesive, LH polymer is selected from a group consisting of polyurethane, polyvinyl chloride homopolymer, polyvinyl chloride-ethylene copolymer, polyvinyl chloride-propylene copolymer, polyvinyl chloride-butylene copolymer, polyvinyl chloride-ethylhexene copolymer, polyvinyl chloride-isoprene copolymer, polyvinyl chloride-butadiene copolymer, polyvinyl chloride-vinyl toluene copolymer, polyvinyl chloride-styrene copolymer, styrene-ethylene copolymer, styrene-propylene copolymer, styrene-butylene copolymer, styrene-ethylhexane copolymer, styrene-isoprene copolymer, styrene-butadiene copolymer, and styrene-butadiene-acrylonitrile terpolymer. The adhesive, LH polymer to be employed in the first LH layer for use in the determination of calcium ion concentration is more preferably selected from the group consisting of polyvinyl chloride-propylene copolymer and styrene-isoprene copolymer.

The LH plasticizer should be compatible in high concentrations with the above described adhesive, LH polymer and should enhance the adhesive characteristics of the polymer. Preferably, the LH plasticizer is selected from a group consisting of adipates, ethers, phosphates, phosphonates, and mixtures thereof. More particularly, the LH plasticizer is selected from the group consisting of nitroaryl alkyl ethers, nitroaryl alkylaryl ethers, nitroaryl arylalkyl ethers, bis(nitroaryl)ethers, nitroaryl aryl ethers, dialkyl alkylphosphonates, dialkyl arylphosphonates, and diaryl arylphosphonates, diaryl alkylphosphonates, trialkyl phosphates, trialkylaryl phosphates, triaryl phosphates, triarylalkyl phosphates, mixtures thereof and at least one of the above in admixture with at least one compound selected from a group consisting of dialkyl adipates, dialkylaryl adipates, diaryl adipates, and diarylalkyl adipates wherein each alkyl group contains from 8-14 carbon atoms and each aryl group contains from 6, 10, or 12 carbon atoms. It is further preferred that each alkyl group contain from 8-12 carbon atoms and be in the normal or iso-alkyl configuration.

More preferably, the plasticizer to be employed in the first LH layer is selected from the group consisting of dioctylphenyl phosphonate and tri(1,1,3,3-tetramethylbutyl)phosphate. Optimally the plasticizer is di-n-octyl phenylphosphonate.

Overlaying the first LH layer and in intimate contact therewith is a second LH layer. This second LH layer comprises an LH polymer having an intrinsic viscosity of from about 1 to about 1.5, preferably from 1 to about 1.3, and more preferably about 1.1 to about 1.2 mg/l; an LH plasticizer; and a calcium ion-selective component.

The LH polymer should be of the type that remains strong and durable even when highly plasticized. Preferably, this LH polymer is a polyvinyl chloride homopolymer.

The LH plasticizer employed in the second layer should possess the same desirable properties as described above with respect to the plasticizer employed in the first LH layer. The preferred plasticizers employed in the second LH layer are also the preferred plasticizer employed in the first LH layer. Furthermore, it is preferred that the same plasticizers be employed in both the first LH layer and the second LH layer.

The ratio of the above described constituents present in the first LH layer and the second LH layer is not critical. However, it is preferred that the first LH layer comprise from about 10 to about 60, preferably from about 15 to about 40, and optimally from about 15 to about 25, weight percent of the adhesive, LH polymer; from about 40 to about 90, more preferably from about 60 to about 85, and optimally about 75 to about 85 weight percent of the LH plasticizer.

With respect to the second LH layer, this layer preferably comprises from about 25 to about 60, more preferably from about 35 to about 45, and optimally about 42.5, weight percent of the LH polymer; from about 30 to about 74.9, more preferably from about 55 to about 65, and optimally about 55, weight percent of the LH plasticizer; and from about 0.1 to about 10, more preferably from about 2 to about 6, and optimally about 2.5, weight percent of the calcium ion-selective component.

The dielectric constants of the first LH layer and the second LH layer are not critical. However, for the determination of calcium it is preferred that the first and second LH layers have a dielectric constant of from about 5 to about 25 at 60 cycles.

The composition of the first LH layer can be prepared, in general, by mixing the adhesive, LH polymer and the LH plasticizer together. To the mixture is added a solvent, such as a 50:50 by volume xylene:1,2-dichloroethane solution. This mixture should be thoroughly and continuously mixed. If desired, one can heat the mixture to about 50° C. to reduce the time required for complete mixing. The mixture is then cooled to room temperature.

The composition of the second LH layer can be prepared, in general, by mixing the LH polymer and the plasticizer together and adding to the mixture a solvent, such as cyclohexanone. This mixture should be thoroughly and continuously mixed. If desired, one can heat the mixture to about 50° C. to reduce the time required for complete mixing. When the mixture has cooled to room temperature, the calcium ion-selective component can be added to the mixture and the mixture again mixed. The calcium ion-selective component can be added as a solution wherein the solvent is, for example, cyclohexanone.

In one preferred embodiment, the first LH layer of the membrane of this invention also comprises the above calcium ion-selective component. In such a case the membrane composition is prepared as discussed above and is added to the reaction mixture after the reaction mixture has cooled to room temperature and the mixture is again mixed. The calcium ion-selective component can be added as a solution wherein the solvent is, for example, cyclohexanone.

The ratio of the constituents present in a calcium ion-selective component containing first LH layer is not critical. However, it is preferred that the calcium ion-selective component containing first LH layer comprise from about 10 to about 60, preferably from about 12.5 to about 40, and optimally from about 14.9 to about 25, weight percent of the adhesive, LH polymer; from about 35 to about 89.99, and more preferably from about 59 to about 87, and optimally from about 74.5 to about 85, weight percent of the LH plasticizer; and from about 0.01 to about 5, more preferably from about 0.05 to about 1, and optimally, from about 0.1 to about 0.5, weight percent of the calcium ion-selective component.

Figure 1:
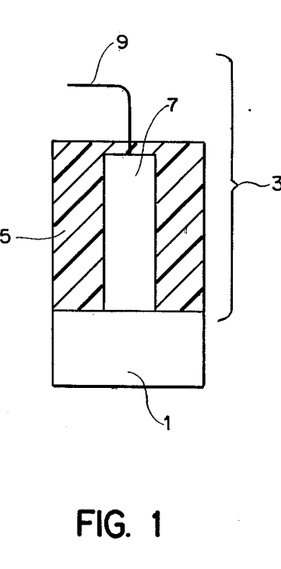
FIG. 1 is a schematic representation of an electrode within the scope of the instant invention.

The membrane of the instant invention can be employed in any electrode known to those skilled in the art. With respect to FIG. 1, a typical electrode comprises a membrane 1 and means 3, including an electrode substrate 7, for electrically connecting the membrane 1 with conductive lead 9, the electrode substrate being located within an insulating stem 5. Examples of electrodes well known to those skilled in the art include, but are not limited to, liquid-junction electrodes, solid state electrodes, ion-selective electrode field effect transistor (ISEFET) electrodes and their corresponding microelectric embodiments.

Figure 2:
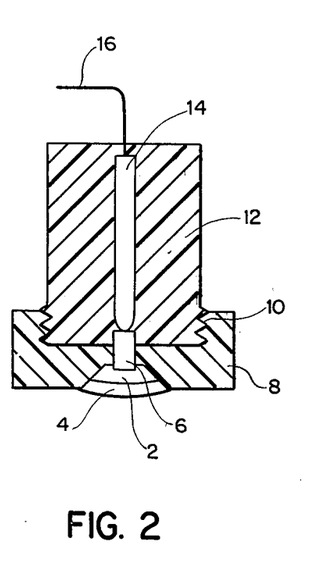
FIG. 2 is a schematic representation of a preferred solid state electrode within the scope of the instant invention.

A preferred solid state electrode embodiment of the instant invention is shown in FIG. 2. An electrically conductive element 6 is firmly held by an electrically insulating cap 8. The cap 8 has means 10 for holding an electrically insulating stem 12 such that electrical conductor 14 is in electrical communication with element 6. Conductor 14 is in electrical communication with electrically conductive lead 16. A first LH layer 2 is in intimate contact with element 6 and a second LH layer 4 is in intimate contact with the first layer 2.

Figure 3:
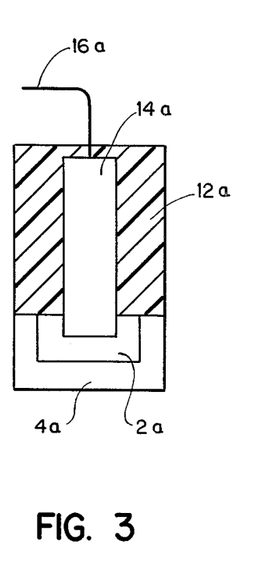
FIG. 3 is a schematic representation of a solid state electrode within the scope of the instant invention.

The lettered numbers of the solid state electrode of FIG. 3 depict another embodiment of the corresponding numbered item discussed with respect to FIG. 2 above. More particularly a first LH layer 2a is in intimate contact with electrical conductor 14a and a second LH layer 4a is in intimate contact with first layer 2a. Conductor 14a is in electrical communication with electrically conductive lead 16a and is located with insulating stem 12a.

Figure 4:
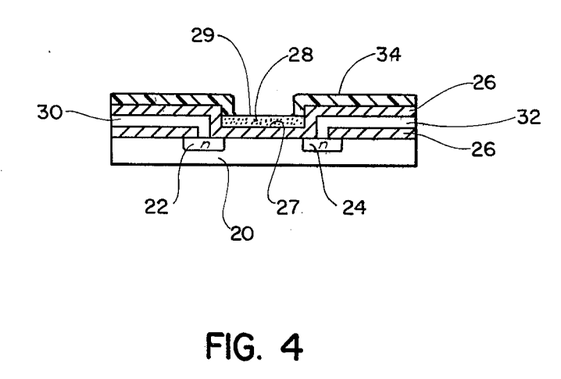
FIG. 4 is a schematic representation of an ISEFET electrode within the scope of the instant invention.

FIG. 4 depicts an ISEFET electrode embodiment of the instant invention. A p-type silicon substrate 20 has two n-type regions, a source diffusion region 22 and a drain diffusion region 24, diffused into the surface of the substrate 20 to a depth, for example, of from one to two microns and spaced twenty microns apart. The ISEFET also includes a thin layer of electrical insulator material 26, such as silicon dioxide, deposited over the substrate 20 and portions of the diffusion regions 22 and 24. Conductive layers 30 and 32, such as aluminum, n-type silicon, etc., are deposited respectively into the source diffusion region 22 and the drain diffusion region 24 to provide electrical contact therewith. A membrane 28 is deposited over the insulator material 26 above the gate region of the ISEFET. Deposition of membrane 28 on the insulator material 26 may be carried out simply by solution casting and may, illustratively, be of a thickness of about 5 microns. Preferably, a layer (not shown) of silicon nitride is deposited between the insulator material 26 and membrane 28 in gate region 27. Since the ISEFET of the instant invention would typically be immersed in or exposed to solutions containing the calcium ion to be assayed, it is desirable that all of the membrane 28 be covered with some type of solution impervious material except for a portion 29 of the membrane which is left exposed for contact with a test solution. Layer 34 represents such material, for example, a polymerized epoxy resin. Although the layer 34 in FIG. 4 is only shown as covering the insulator material 26 and a portion of the membrane 28, it should be understood that the solution impervious material would cover all parts of the device including electrical leads, etc., which might be immersed in the solution except for the exposed portion 29. The type of solution impervious material used, of course, would depend upon the kinds of solution into which the ISEFET is to be immersed, but generally, the material should be at least water impervious and preferably biocompatible, i.e., should not adversely interact with the solution of tissue to which the device is exposed.

The electrodes of the instant invention can be fabricated in a number of different ways depending on a desired configuration as well as one's manufacturing capabilities. For example, if a solid state electrode such as shown in FIG. 2 is desired, the first LH layer is formed by placing a predetermined amount of the mixture of the composition of the first layer over element and drying the coated element a room temperature. If desired, this sequence can be repeated more than once. Over the dried first layer is placed a predetermined amount of the mixture of the composition of the second layer and also dried at room temperature. If desired, this latter sequence can also be repeated more than one time, and preferably is repeated at least once.

The electrodes within the scope of this invention can be employed to determine calcium ion concentration in any suitable solution. The solution can, for example, be water, biological fluids, such as blood and urine, aqueous solutions, such as wine and beer, and numerous other liquids and environments wherein one desires to perform such end measurement.

The following examples are provided for the purpose of further illustration only and are not intended to be limitations on the disclosed invention.

EXAMPLE 1

Synthesis of N-Ethyl-Morpholinium Salt of Dioctylphenyl Acid Phosphate

A. To a 500 ml separatory funnel was added via a powder funnel a weighed amount (about 40 gm) of octylphenyl acid phosphate from Mobil Chemical Co. (reported to be a 70/30 mixture of the di/mono-estes $((RO)_2POOH$ and $(RO)PO(OH)_2$, respectively, wherein R is $C_8H_{17}C_6H_4$—). Next, 200 ml of dry heptane was added to the separatory funnel. The separatory funnel was then stoppered and shaken to dissolve the crude octylphenyl phosphate. (A portion of the octylphenyl phosphate, thought to be the monoester phosphate, did not completely dissolve.)

B. To the contents present in the separatory funnel were then added 200 ml ethylene glycol (c.p.). The separatory funnel was restoppered and shaken vigorously to extract the more glycolsoluble monoester phosphate from the diester phosphate (which remained in the heptane layer). The two layers were allowed to completely separate and then the bottom glycol layer was drawn off.

C. A fresh portion (200 ml) of ethylene glycol was added to the separatory funnel. The separatory funnel and its contents were shaken vigorously for several minutes and then allowed to stand until the layers separated clearly. The glycol layer was once again carefully drawn off.

D. Step C was repeated three more times.

E. To the separatory funnel was now added 150 ml of 0.1 M HCl. The separatory funnel and its contents were shaken vigorously and then allowed to stand until the layers separated clearly. The acid layer was drawn off and this dilute acid wash step was repeated one more time.

F. After carefully removing all the aqueous acid from the heptane layer at the bottom of the separatory funnel, approximately 40 gms of anhydrous sodium sulfate powder was added directly to the separatory funnel and the heptane contents. The heptane and sodium sulfate were vigorously mixed together for a few minutes and then allowed to stand (after relieving any internal pressure build-up) in the funnel for another 10–15 minutes.

G. To remove all the sodium sulfate from the heptane, the heptane from step F was then poured from the top of the separatory funnel into a medium pore fritted glass Büchner funnel.

H. While stirring the dry filtered heptane, 10 ml of N-ethyl morpholine was added. The stirring was continued for a few minutes after complete addition of the N-ethyl morpholine. The container was covered and stirred for about an hour. A somewhat slow crystallization of the diester phosphate morpholinium quaternary salt formed and precipitated over this period.

I. The white crystalline precipitate was filtered in a fritted Büchner funnel under vacuum and rinsed once with about 100 ml of chilled heptane thereafter.

J. The white precipitate was vacuum dried for several hours and then placed in an amber bottle and capped and weighed to determine the yield of the diester product.

K. Calculations 40.87g of Mobil brand Octylphenyl acid phosphate
22.06 g of dry white precipitate from (J) above
$$\frac{474 \text{ (M.W. of free diester)}}{589 \text{ (M.W. of Morpholide Diester)}} = \frac{X}{22.05 \text{ g of dry ester morpholide}} \text{ actual free diester}$$
$X = 17.76$ g of free diester actually isolated (as morpholineum salt)

The Mobil brand octylphenyl acid phosphate mixture is stated to be 70/30 of diester to monoester. Thus, 40.87 g of mixture should yield $40.87 \times 0.7 = 28.6/g$ of free acid diester phosphate, therefore:

$$\frac{17.76 \text{ actually isolated}}{28.61 \text{ theoretical expected}} \times 100 = 62.08\%$$
Recovery of Diester.

EXAMPLE 2

Compounding of Composition for Layer 2 Devoid of Calcium Ionophore

A. Flowell 470 brand polyvinyl chloride-propylene copolymer (1.8 gm) was weighed out into a 60 ml capacity wide mouth amber bottle equipped with a polyseal cap.

B. Dioctyl phenylphosphonate (8.2 gm) was added to the polyvinyl chloride-propylene copolymer and the two ingredients were then mixed, thereby forming a slurry.

C. Finally, 35 ml of a 50/50 by volume xylene/dichloroethane solvent was added to the above slurry.

D. The bottle was quickly closed and vigorously shaken and then placed on a roll mixer and continuously mixed under a 50° C. heat lamp until all the ingredients had clearly dissolved.

EXAMPLE 3

Compounding of Another Composition for Layer 2 Devoid of Calcium Ionophore

The procedure set forth in Example 2 was employed with the sole modification being the substitution of a 50/50 by volume (8.2 gm) mixture of dioctyl adipate and dioctyl phenylphosphonate for the 8.2 gm of dioctyl phenylphosphonate used therein.

EXAMPLE 4

Compounding a Calcium Ionophore Containing Composition of Layer 2

The procedure set forth in Example 2 was employed with the following modifications:

1. 8.1 gm of dioctyl phenylphosphonate was employed instead of 8.2 gm;
2. After step B, 0.1 gm of N-ethyl-morpholinium salt of dioctylphenyl phosphoric acid (EM.HDOPP) was added to the slurry formed in step B and the resulting mixture thoroughly mixed.

EXAMPLE 5

Compounding Another Calcium Ionophore Containing Composition for Layer 2

The procedure set forth in Example 4 was employed with the sole modification being the substitution of a 50/50 by volume (8.1 gm) mixture of dioctyl adipate and dioctyl phenylphosphonate for the 8.1 gm of dioctyl phenylphosphonate used therein.

EXAMPLE 6

Compounding of Composition for Layer 4

A. Geon 102EPF5 brand polyvinyl chloride homopolymer (4.25 gm) was weighed out into a 60 ml capacity wide mouth amber bottle equipped with a polyseal cap.

B. Dioctyl phenylphosphonate (5.5 gm) was added to the polyvinyl chloride homopolymer and the two ingredients were then mixed thereby forming a slurry.

C. Next, 0.25 gm EM"DOPP was added to the above slurry and the resulting slurry-mixture thoroughly mixed.

D. Finally, 40 ml of cyclohexanone solvent was added to this slurry mixture.

E. The bottle was quickly closed and vigorously shaken and then placed on a roll mixer and continuously mixed under a 50° C. heat lamp until all the ingredients had clearly dissolved.

EXAMPLE 7

Fabrication of Membrane

A cap of the type schematically shown in FIG. 2 as numeral 8 having firmly held therein an element comprising a compacted mixture of silver-silver chloride was selected. The composition (35 ml) prepared in Example 2 was then deposited over the element and allowed to dry at room temperature for about 24 hours. Next, 35 ml of the composition prepared in Example 6 was then deposited over the first layer and also allowed to dry at room temperature for 24 hours. A second 35 ml aliquot of the composition prepared in Example 6 was deposited over the previously dried layers and allowed to dry in air for an additional 72 hours.

EXAMPLE 8

Life Span

Figure 5:
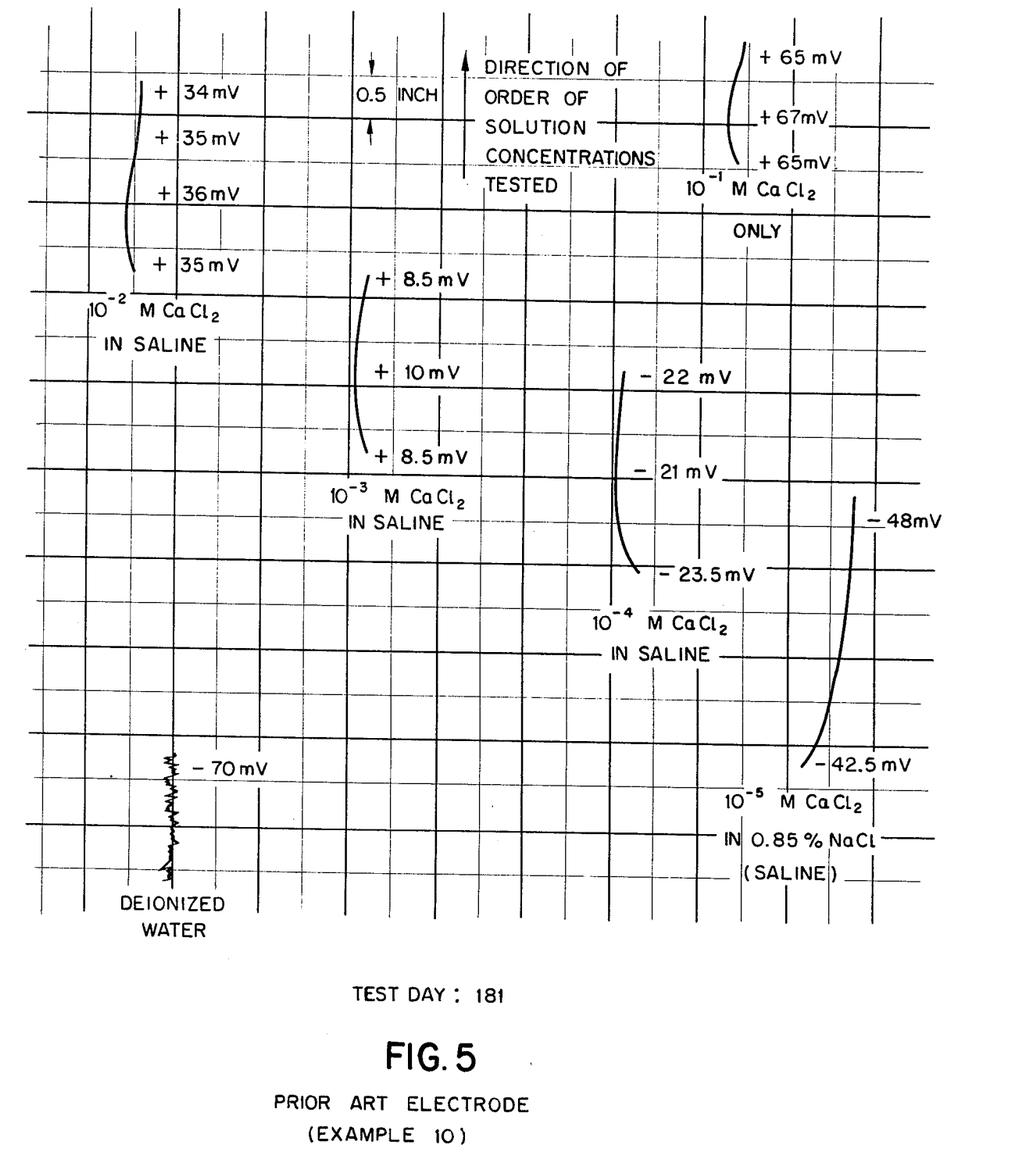
FIG. 5 is a chart recording of a prior art electrode.

The solid state electrode prepared in Example 7 was evaluated for Nernstian activity and the data obtained therefrom is shown in Table I.

per minute. FIG. 5 graphically depicts the failure of electrode Z to reach a steady state at any of the 5 calcium concentrations tested even after a lapse of several minutes at each calcium concentration, thereby making it difficult for one to obtain a precise quantitative answer.

Figure 6:
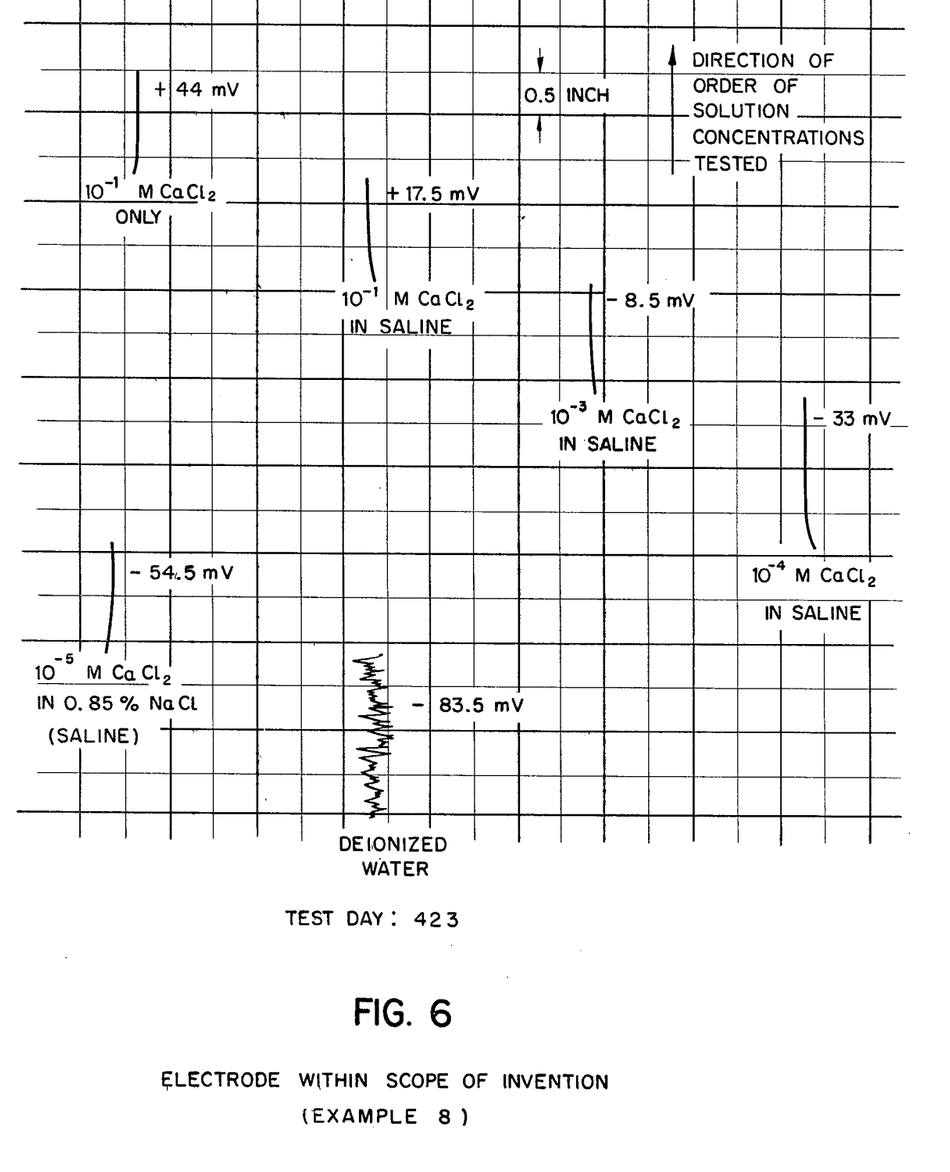
FIG. 6 is a chart recording of an electrode within the scope of the instant invention.

In sharp contrast, FIG. 6 depicts a chart recording of an electrode (prepared in Example 7 and evaluated for

TABLE I

ELECTRODE LIFE SPAN FOR CALCIUM ELECTRODE

| Day | Moles/Liter (M/l) vs. Millivoltage (mV) | | | | | Span (mV) per Decade | | | |
|---|---|---|---|---|---|---|---|---|---|
| | $10^{-5}$ M/l | $10^{-4}$ M/l | $10^{-3}$ M/l | $10^{-2}$ M/l | $10^{-1}$ M/l | $10^{-5}$–$10^{-4}$ M/l | $10^{-4}$–$10^{-3}$ M/l | $10^{-3}$–$10^{-2}$ M/l | $10^{-2}$–$10^{-1}$ M/l |
| DATA FOR ELECTRODE WITHIN SCOPE OF INSTANT INVENTION (EXAMPLE 8) | | | | | | | | | |
| 1 | −72 | −45 | −16 | +12.5 | +42 | 27 | 29 | 28.5 | 29.5 |
| 2 | −70 | −41.5 | −9.5 | +22 | +55 | 28.5 | 32 | 31.5 | 33 |
| 162 | −34 | −5.5 | +21.5 | +56 | +85 | 28.5 | 27 | 34.5 | 29 |
| 367 | −40 | −9.5 | +17.5 | +44.5 | +75 | 30.5 | 27 | 27 | 30.5 |
| 382 | −35 | −13 | +13.5 | +41 | +70.5 | 22 | 26.5 | 27.5 | 29.5 |
| 414 | −49.5 | −24 | +0.5 | +23 | +49 | 25.5 | 24.5 | 23.5 | 26.5 |
| 423 | −54.5 | −33 | −8.5 | +17.5 | +44 | 21.5 | 24.5 | 26 | 26.5 |
| DATA FOR PRIOR ART ELECTRODE (EXAMPLE 9) | | | | | | | | | |
| 1 | −27 | −16.5 | +7.5 | +34.5 | N/A[1] | 10.5 | 24.5 | 29.5 | N/A |
| 9 | −23 | −10.5 | +13 | +40 | N/A | 12.5 | 23.5 | 27.5 | N/A |
| 10 | +79 | +92.5 | +115.5 | +141.5 | N/A | 13 | 24 | 26 | N/A |
| 104 | +10 | +9 | +11 | N/A | N/A | 1 | 2 | N/A | N/A |
| DATA FOR PRIOR ART ELECTRODE (EXAMPLE 10) | | | | | | | | | |
| 1 | −47.5 | −30 | −2 | +28 | +59 | 17.5 | 28 | 30 | 31 |
| 49 | −54.5 | −33 | −8.5 | +17.5 | +44 | 21.5 | 29.5 | 26.5 | 29.5 |
| 110 | −45 | −30.5 | −1 | +27 | +57 | 14.5 | 29.5 | 28 | 30 |
| 181 | −42.5 | −23.5 | +8.5 | +35 | +65 | 19 | 32 | 26.5 | 30 |

[1]N/A denotes not available.
[2]Data indicates that electrode failure occurred some time between the 10th day and the 104th day.

The electrode within the scope of the instant invention was periodically evaluated over a fourteen month span including continuous use during a three month period therein. Although the activity of the electrode declined from its earlier performance, the electrode still exhibited suitable performance thereby enabling its continued use beyond the first fourteen month period.

EXAMPLE 9

A prior art Orion Research, Inc. 93-20 brand calcium electrode (hereinafter referred to as Y) was evaluated for Nernstian activity and the data obtained therefrom is also set forth in Table I.

In addition to an unsatisfactory span per decade in the $10^{-5}$–$10^{-4}$ M/l range, calcium electrode Y failed to respond to changes in calcium concentration less than 4 months after intermittent use.

EXAMPLE 10

A prior art HNU System, Inc. ISE 20-20-00 brand calcium electrode (hereinafter referred to as Z) was evaluated for Nernstian activity and the data obtained therefrom is also set forth in Table I.

Although it exhibited a satisfactory span per decade response over most calcium concentration ranges, calcium electrode Z exhibited an unsatisfactory span per decade in the $10^{-5}$–$10^{-4}$ M/l range. This shortcoming is significant in that an electrode must exhibit a suitable span in this low concentration range if it is to be suitable for use when microsampling is required, e.g., in medical diagnostic areas such as the diagnosis of premature infants.

Another shortcoming of calcium electrode Z is its slow and non-steady response to calcium concentrations. This fact can be seen in FIG. 5 which is a copy of a chart recording of calcium electrode Z for various calcium concentrations. The chart speed was 0.5 inch per minute. FIG. 5 graphically depicts the failure of electrode Z to reach a steady state at any of the 5 calcium concentrations tested even after a lapse of several minutes at each calcium concentration, thereby making it difficult for one to obtain a precise quantitative answer.

Nernstian activity in Example 8) within the scope of the instant invention. The chart speed was also 0.5 inches per minute. FIG. 6 graphically depicts the fact that electrodes within the scope of the instant invention quickly (i.e., within a few seconds) reach and hold a steady state at each of the 5 calcium concentrations tested. This property makes the electrodes of the instant invention highly suitable for use in automated equipment wherein it is essential to quickly arrive at a steady state. Furthermore, one using an electrode within the scope of the instant invention would also have a higher confidence level in the accuracy of the data obtained therefrom because of the lack of drift present in the electrode.

Based on this disclosure, many other modifications and ramifications will naturally suggest themselves to those skilled in the art of ion-selective electrodes. These are intended to be comprehended as within the scope of this invention.

BIBLIOGRAPHY

1. Koryta, *Analytica Chimica Acta*, 61:329–411 (1972).
2. Buck, *Analytical Chemistry*, 46(5):28R–51R (1974).
3. Koryta, *Analytica Chimica Acta*, 91:1–85 (1977).
4. Buck, *Analytical Chemistry*, 50(5):17R–29R (1978).
5. U.S. Pat. No. 3,429,785.
6. U.S. Pat. No. 3,448,032.
7. U.S. Pat. No. 3,691,047.
8. U.S. Pat. No. 3,729,401.
9. U.S. Pat. No. 3,856,649.
10. U.S. Pat. No. 3,932,233.
11. Moody et al., *Analyst*, 95:910–918 (1970.
12. Cattrall et al., *Analyticali Chemistry*, 43(13):1905–1906 (1971).
13. Griffiths et al., *Analyst*, 97:420–427 (1972).
14. Subryan et al., *Clinical Chemistry*, 18(12): 1459–1462 (1972).

15. Ruzicka et al., *Analytica Chimica Acta*, 67:155–178 (1973).
16. Morf et al., *Analytical Letters*, 7(1):9–22 (1974).
17. Thomas, *Proc. Soc. Analyt. Chem.*, 340—342 (December, 1974).
18. Pretsch et al., *Research Development*, 20–24 (March, 1974).
19. Cattrall et al., *Analytica Chimica Acta*, 76:269–277 (1975).
20. Schwartz, *Clinica Chimica Acta*, 64:277–239 (1975).
21. Ammann et al., *Analyticali Letters*, 8(10):709–720 (1975).
22. Fuchs et al., *Clinica Chimica Acta*, 67:99–102 (1976).
23. Schwartz, *Clin. Chem.*, 22(4):461–467 (1976).
24. Hulanicki et al., *Analytica Chimica Acta*, 87:411–417 (1976).
25. Owen et al., *Analytica Chimica Acta*, 90:241–244 (1977).
26. Fuchs et al. and Schwartz, *Clinical Chemistry*, 23(3):610–611 (1977).
27. Craggs et al., *Analyst*, 104:412–418 (1979).
28. Partridge et al., *J. Inorg. Nucl. Chem.*, 31:2587–2589 (1969).
29. Griffiths et al., *J. Inorg. Nucl. Chem.*, 34:3043–3048 (1972).
30. Moody et al., *Analyst*, 103:68–71 (1978).

The embodiments of the invention in which an exclusive property or privilege is claimed are defined as follows:

1. A membrane for use in the determination of calcium ion concentration in an aqueous solution, said membrane being of the type comprising a calcium ion selective component and a carrier material, characterized in that said calcium ion selective component is a compound having a formula wherein
X and Y are selected from a group consisting of aryl, alkyl(aryl) alkenyl, cycloalkenyl, and alkynyl radicals wherein said alkyl moiety of said alkyl(aryl) radical consists of 1–12 carbon atoms; each alkenyl and alkynyl moiety of said alkenyl(aryl) and alkynyl(aryl) radicals, respectively, consists of 2–12 carbon atoms; each aryl moiety consists of 6, 10, 12, or 14 carbon atoms; and each alkyl, cycloalkyl, alkenyl, cycloalkenyl, and alkynyl radical consists of 6 to 14 carbon atoms; and
Z is selected from a group consisting of alkyl radicals containing 1–12 carbon atoms; alkenyl and alkynyl radicals containing 4–12 carbon atoms; and cycloalkyl and cycloalkenyl radicals containing 6 to 12 carbon atoms.

2. The membrane of claim 1 wherein X and Y are the same.

3. The membrane of claim 2 wherein X and Y are an aryl radical.

4. The membrane of claim 2 wherein X and Y are selected from the group consisting of alkyl(aryl), alkenyl(aryl), and alkynyl(aryl) radicals.

5. The membrane of claim 4 wherein X and Y are selected from the group consisting of (t-butyl)phenyl, (t-butyl)diphenyl, (t-butyl)naphthyl, (n-octyl)phenyl, (iso-octyl)phenyl, (t-octyl)phenyl, ((t-octyl)naphthyl, (methyl)phenyl, (ethyl)phenyl, (n-propyl)phenyl, (iso-propyl)phenyl, (n-butyl)phenyl, (iso-butyl)phenyl, (n-pentyl)phenyl, (n-hexyl)phenyl, (1,2-dimethylbutyl)phenyl, (2-ethylhexyl)phenyl, (iso-nonyl)phenyl, (n-decyl)phenyl, (iso-decyl)phenyl, and (n-dodecyl)phenyl.

6. The membrane of claim 5 wherein X and Y are selected from a group consisting of p-(1,1,3,3-tetramethylbutyl)phenyl, p-(iso-decyl)phenyl, p-(n-decyl)phenyl, p-(2-ethylhexyl)phenyl, and p-(n-octyl)phenyl.

7. The membrane of claim 2 wherein X and Y are selected from the group consisting of alkyl, cycloalkyl, alkenyl, cycloalkenyl, and alkynyl radicals.

8. The membrane of claim 7 wherein X and Y are selected from the group consisting of cyclohexyl, cyclooctyl, cyclooctenyl, octylenyl-1, cyclododecyl, dodecenyl-1, t-butyl, 3-butenyl, n-octyl, iso-octyl, t-octyl, methyl, ethyl, n-propyl, iso-propyl, n-butyl, iso-butyl, n-pentyl, n-hexyl, 1-heptynyl, 1,2-dimethylbutyl, 2-ethylhexyl, iso-nonyl, n-decyl, iso-decyl, and n-dodecyl.

9. The membrane of claim 8 wherein X and Y are selected from the group consisting of n-octyl, iso-nonyl, n-dodecyl, n-decyl, and iso-decyl.

10. The membrane of claims 1–8 or 9 wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl.

11. The membrane of claims 1–8 or 9 wherein Z is ethyl.

12. The membrane of claim 1 comprising:
(a) a first lipophilic-hydrophobic layer comprising:
  (i) an adhesive, lipophilic-hydrophobic polymer having an intrinsic viscosity of from about 0.4 to about 0.9 ml/g; and
  (ii) a lipophilic-hydrophobic plasticizer; and
(b) a second lipophilic-hydrophobic layer in intimate contact with said first layer, said second layer comprising:
  (i) a lipophilic-hydrophobic polymer having an intrinstic viscosity of from about 1 to about 1.5 ml/g;
  (ii) a lipophilic-hydrophobic plasticizer; and
  (iii) said calcium ion-selective component.

13. The membrane of claim 12 wherein:
(a) said adhesive, lipophilic-hydrophobic polymer present in said first layer is selected from a group consisting of polyvinyl chloride-propylene copolymer and styrene-isoprene copolymer;
(b) said lipophilic-hydrophobic polymer present in said second layer is polyvinyl chloride homopolymer; and
(c) said lipophilic-hydrophobic plasticizer is selected from a group consisting of nitroaryl alkyl ethers, nitroaryl alkylaryl ethers, nitroaryl arylalkyl ethers, bis(nitroaryl)ethers, nitroaryl aryl ethers, dialkyl alkylphosphonates, dialkyl arylphosphonates, diaryl arylphosphonates, diaryl alkylphosphonates, trialkyl phosphates, trialkylaryl phosphates, triaryl phosphates, triarylalkyl phosphates, mixtures thereof and at least one of the above in admixture with at least one compound selected from a group consisting of dialkyl adipates, dialkylaryl adipates, diaryl adipates, and diarylalkyl adipates, wherein each alkyl group contains from 8 to 14 carbon atoms and each aryl group contains 6, 10, or 12 carbon atoms.

14. The membrane of claim 13 wherein said first layer comprises from about 10 to about 60 weight percent of said adhesive lipophilic-hydrophobic polymer and from about 40 to about 90 weight percent of said lipophilic-hydrophobic plasticizer; and said second layer comprises from about 25 to about 60 weight percent of said polyvinyl chloride homopolymer, from about 30 to about 74.9 weight percent of said lipophilic-hydrophobic plasticizer; and from about 0.1 to about 10 weight percent of said calcium ion selection component.

15. The membrane of claim 14 wherein said first layer comprises from about 15 to about 40 weight percent of said adhesive, lipophilic-hydrophobic polymer and from about 60 to about 85 weight percent of said lipophilic-hydrophobic plasticizer; and said second layer comprises from about 35 to about 45 weight percent of said polyvinyl chloride homopolymer, from about 55 to about 65 weight percent of said lipophilic-hydrophobic plasticizer, and from about 2 to about 6 weight percent of said calcium ion selective component.

16. The membrane of claim 15 wherein said first layer comprises from about 15 to about 25 weight percent of said adhesive, lipophilic-hydrophobic polymer and from about 75 to about 85 weight percent of said lipophilic-hydrophobic plasticizer; and said second layer comprises about 42.5 weight percent of said polyvinyl chloride homopolymer, about 55 weight percent of said lipophilic-hydrophobic plasticizer, and about 2.5 weight percent of said calcium ion selective component.

17. The membrane of claim 16 wherein said adhesive lipophilic-hydrophobic polymer in said first layer has an intrinsic viscosity of from about 0.5 to about 0.7 ml/g, wherein each of said alkyl groups contains from 8 to 12 carbon atoms; and wherein said polyvinyl chloride homopolymer has an intrinsic viscosity of from about 1 to about 1.3 ml/g.

18. The membrane of claim 17 wherein said adhesive, lipophilic-hydrophobic polymer in said first layer has an intrinsic viscosity of from about 0.6 ml/g; wherein said lipophilic-hydrophobic plasticizer in said first and second layer is the same; and wherein said polyvinyl chloride homopolymer has an intrinsic viscosity of from about 1.1 to about 1.2 ml/g.

19. The membrane of claim 18 wherein said lipophilic-hydrophobic plasticizer is dioctyl phenylphosphonate.

20. The membrane of claims 12-18 or 19 wherein X and Y are are the same and are an aryl radical; and wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl.

21. The membrane of claims 12-18 or 19 wherein X and Y are the same and are selected from the group consisting of alkyl(aryl), alkenyl(aryl), and alkynl(aryl) radicals.

22. The membrane of claims 12-18 or 19 wherein X and Y are the same and are selected from the group consisting of (t-butyl)phenyl, p-(t-butyl)diphenyl, (t-butyl)naphthyl, (n-octyl)-phenyl, (iso-octyl)phenyl, (t-octyl)phenyl, (t-octyl)naphthyl, (methyl)phenyl, (ethyl)phenyl, (n-propyl)phenyl, (isopropyl)phenyl, (n-butyl)-phenyl, (iso-butyl)phenyl, (n-pentyl)phenyl, (n-hexyl)phenyl, (1,2-dimethylbutyl)phenyl, (2-ethylhexyl)phenyl, (iso-nonyl)phenyl, (n-decyl)phenyl, (iso-decyl)phenyl, and (n-dodecyl)phenyl; and wherein Z is selected from a group consisting of cyclohexyl, cyclooctyl, cyclooctenyl, octenyl-1, cyclododecyl, dodecenyl-1, t-butyl, 3-butenyl, n-octyl, t-octyl, 1-heptynyl, methyl, ethyl, n-propyl, iso-propyl, n-butyl, sec-butyl, n-pentyl, n-hexyl, 1,2-dimethylbutyl, 2-ethylhexyl, n-decyl, and n-dodecyl.

23. The membrane of claims 12-18 or 19 wherein X and Y are the same and are selected from a group consisting of p-(1,1,3,3-tetramethylbutyl)phenyl, p-(iso-decyl)phenyl, p-(n-decyl)phenyl, p-(2-ethylhexyl)phenyl, and p-(n-octyl)phenyl; and wherein Z is ethyl.

24. The membrane of claims 12-18 or 19 wherein X and Y are the same and wherein X and Y are selected from the group consisting of alkyl, cycloalkyl, alkenyl, cycloalkenyl, and alkynyl radicals.

25. The membrane of claims 12-18 or 19 wherein X and Y are the same and are selected from the group consisting of cyclohexyl, cyclooctyl, cyclooctenyl, octenyl-1, cyclododecyl, dodecenyl-1, t-butyl, 3-butenyl, n-octyl, iso-octyl, t-octyl, methyl, ethyl, n-propyl, iso-propyl, n-butyl, iso-butyl, n-pentyl, n-hexyl, 1,2-dimethylbutyl, 2-ethylhexyl, iso-nonyl, n-decyl, iso-decyl, and n-dodecyl; and wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl.

26. The membrane of claims 12-18 or 19 wherein X and Y are the same and are selected from the group consisting of n-octyl, iso-nonyl, n-dodecyl, oleyl, n-decyl, and iso-decyl; and wherein Z is ethyl.

27. The membrane of claim 1 comprising:
(a) a first lipophilic-hydrophobic layer comprising:
  (i) an adhesive, lipophilic-hydrophobic polymer having an intrinsic viscosity of from about 0.2 to about 0.9 ml/g;
  (ii) a lipophilic-hydrophobic plasticizer; and
  (iii) said calcium ion-selective component; and
(c) a second lipophilic-hydrophobic layer in intimate contact with said first layer, said second layer comprising:
  (i) a lipophilic-hydrophobic polymer having an intrinsic viscosity of from about 1 to about 1.5 ml/g;
  (ii) a lipophilic-hydrophobic plasticizer; and
  (iii) said calcium ion-selective component.

28. The membrane of claim 27 wherein:
(a) said adhesive, lipophilic-hydrophobic polymer present in said first layer is selected from a group consisting of polyvinyl chloride-propylene homopolymer and styrene-isoprene copolymer;
(b) said lipophilic-hydrophobic polymer present in said second layer is polyvinyl chloride homopolymer; and
(c) said lipophilic-hydrophobic plasticizer is selected froma first group consisting of nitroaryl alkyl ethers, nitroaryl alkyl ethers, nitroaryl arylalkyl ethers, bis(nitroaryl)ethers, nitroarylaryl ethers, dialkyl alkyl phosphonates, dialkyl arylphosphonates, diaryl arylphosphonates, diaryl alkylphosphonates, trialkyl phosphates, trialkylaryl phosphates, triaryl phosphates, triarylalkyl phosphates, mixtures thereof and at least one of the above in admixture with at least one compound selected from a group consisting of dialkyl adipates, dialkylaryl adipates, diaryl adipates, and diarylalkyl adipates, wherein each alkyl group contains from about 8 to about 14 carbon atoms and each aryl group contains 6, 10, or 12 carbon atoms.

29. The membrane of claim 28 wherein said first layer comprises from about 10 to about 60 weight percent of said adhesive lipophilic-hydrophobic polymer, from about 35 to about 89.99 weight percent of said lipophilic-hydrophobic plasticizer, and from about 0.01 to about 5 weight percent of said calcium selective component; and said second layer comprises from about 25 to about 60 weight percent of said polyvinyl chloride homopolymer, from about 30 to about 74.9 weight percent of said lipophilic-hydrophobic plasticizer; and from about 0.1 to about 10 weight percent of said calcium selective component.

30. The membrane of claim 29 wherein said first layer comprises from about 12.5 to about 40 weight percent of said adhesive, lipophilic-hydrophobic polymer, from about 59 to about 87 weight percent of said lipophilic-hydrophobic plasticizer, and from about 0.05 to about 1 weight percent of said calcium selective component; and said second layer comprises from about 35 to about 45 weight percent of said polyvinyl chloride homopolymer, from about 55 to about 65 weight percent of said lipophilic-hydrophobic plasticizer, and from about 2 to about 6 weight percent of said calcium selective component.

31. The membrane of claim 31 wherein said first layer comprises from about 14.9 to about 25 weight percent of said adhesive, lipophilic-hydrophobic polymer from about 74.5 to about 85 weight percent of said lipophilic-hydrophobic plasticizer, and from about 0.1 to about 0.5 weight percent of said calcium selective component; and said second layer comprises about 42.5 weight percent of said polyvinyl chloride homopolymer, about 55 weight percent of said lipophilic-hydrophobic plasticizer, and about 2.5 weight percent of said calcium selective component.

32. The membrane of claim 31 wherein said adhesive lipophilic-hydrophobic polymer in said first layer has an intrinsic viscosity of from about 0.5 to about 0.7 ml/g, wherein each of said alkyl groups contains from 8 to 12 carbon atoms; and wherein said polyvinyl chloride homopolymer has an intrinsic viscosity of from about 1.0 to about 1.3 ml/g.

33. The membrane of claim 32 wherein said adhesive, lipophilic-hydrophobic polymer in said first layer has an intrinsic viscosity of about 0.6 ml/g; wherein said lipophilic-hydrophobic plasticizer in said first and second layer is the same; and wherein said polyvinyl chloride homopolymer has an intrinsic viscosity of from about 1.1 to about 1.2 ml/g.

34. The membrane of claim 33 wherein said lipophilic-hydrophobic plasticizer is dioctyl phenylphosphonate.

35. The membrane of claims 27–33 or 34 wherein X and Y are the same and are an aryl radical; and wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl.

36. The membrane of claims 27–33 or 34 wherein X and Y are the same and are selected from the group consisting of alkyl(aryl), alkenyl(aryl), and alkynl(aryl) radicals.

37. The membrane of claims 27–33 or 34 wherein X and Y are the same and are selected from the group consisting of (t-butyl)phenyl, p-(t-butyl)diphenyl, (t-butyl)naphthyl, (n-octyl)-phenyl, (iso-octyl)phenyl, (t-octyl)phenyl, (t-octyl)naphthyl, (methyl)phenyl, (ethyl)phenyl, (n-propyl)phenyl, (iso-propyl)phenyl, (n-butyl)-phenyl, (iso-butyl)phenyl, (n-pentyl)phenyl, (n-hexyl)phenyl, (1,2-dimethylbutyl)phenyl, (2-ethylhexyl)phenyl, (iso-nonyl)phenyl, (n-decyl)phenyl, (iso-decyl)phenyl, and (n-dodecyl)phenyl; and wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl.

38. The membrane of claims 27–33 or 34 wherein X and Y are the same and are selected from a group consisting of p-(1,1,3,3-tetramethylbutyl)phenyl, p-(iso-decyl)phenyl, p-(n-decyl)phenyl, p-(2-ethylhexyl)phenyl, and p-(n-octyl)phenyl; and wherein Z is ethyl.

39. The membrane of claims 27–33 or 34 wherein X and Y are the same and wherein X and Y are selected from the group consisting of alkyl, cycloalkyl, alkenyl, cycloalkenyl, and alknyl radicals.

40. The membrane of claims 27–33 or 34 wherein X and Y are the same; wherein X and Y are selected from the group consisting of cyclohexyl, cyclooctyl, cyclooctenyl, octenyl-1, cyclododecyl, dodecenyl-1, t-butyl, 3-butenyl, n-octyl, iso-octyl, t-octyl, methyl, ethyl, n-propyl, iso-propyl, n-butyl, iso-butyl, n-pentyl, n-hexyl, 1,2-dimethylbutyl, 2-ethylhexyl, iso-nonyl, n-decyl, iso-decyl, and n-dodecyl; and wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl.

41. The membrane of claims 27–33 or 34 wherein X and Y are the same; wherein X and Y are selected from the group consisting of n-octyl, iso-nonyl, n-dodecyl, oleyl, n-decyl, and iso-decyl; and wherein Z is ethyl.

42. An improved electrode of the type comprising a membrane and means, including an electrode substrate, for electrically connecting the membrane with a conductive lead, characterized in that said membrane is the membrane of claim 1.

43. The electrode of claim 42 whrein X and Y are the same.

44. The electrode of claim 43 wherein X and Y are selected from the group consisting of (t-butyl)phenyl, p-(t-butyl)diphenyl, (t-butyl)naphthyl, (n-octyl)phenyl, (iso-octyl)phenyl, (t-octyl)phenyl, (t-octyl)naphthyl, (methyl)phenyl, (ethyl)phenyl, (n-propyl)phenyl, (iso-propyl)phenyl, (n-butyl)phenyl, (iso-butyl)phenyl, (n-pentyl)phenyl, (n-hexyl)phenyl, (1,2-dimethylbutyl)phenyl, (2-ethylhexyl)phenyl, (iso-nonyl)phenyl, (n- decyl)phenyl, (iso-decyl)phenyl, and (n-dodecyl)phenyl.

45. The electrode of claim 44 wherein X and Y are selected from a group consisting of p-(1,1,3-tetramethylbutylphenyl, p-(iso-decyl)phenyl, p-(n-decyl)phenyl, (2-ethylhexyl)phenyl, and p-(n-octylphenyl.

46. The electrode of claim 45 wherein X and Y are selected from the group consisting of cyclohexyl, cyclooctyl, cyclooctenyl, octenyl-1, cyclododecyl, dodecenyl-1, oleyl, t-butyl, 3-butenyl, n-octyl, iso-octyl, t-octyl, methyl, ethyl, n-propyl, iso-propyl, n-butyl, iso-butyl, n-pentyl, n-hexyl, 1-heptynyl, 1,2-dimethylbutyl, 2-ethylhexyl, iso-nonyl, n-decyl, iso-decyl, and n-dodecyl.

47. The electrode of claim 46 wherein X and Y are selected from the group consisting of n-octyl, iso-nonyl, n-dodecyl, oleyl, n-decyl, and iso-decyl.

48. The electrode of claims 42–46 or 47 wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl.

49. The electrode of claims 42–46 or 47 wherein Z is ethyl.

50. The electrode of claim 42 wherein said membrane comprises:
(a) a first lipophilic-hydrophobic layer comprising:
   (i) an adhesive, lipophilic-hydrophobic polymer having an intrinsic viscosity of from about 0.4 to about 0.9 ml/g; and
   (ii) a lipophilic-hydrophobic plasticizer; and
(c) a second lipophilic-hydrophobic layer in intimate contact with said first layer, said second layer comprising:
   (i) a lipophilic-hydrophobic polymer having an intrinsic viscosity of from about 1 to about 1.5 ml/g;
   (ii) a lipophilic-hydrophobic plasticizer; and
   (iii) said calcium ion selective component.

51. The electrode of claim 50 wherein:
(a) said adhesive, lipophilic-hydrophobic polymer present in said first layer is selected from a group consisting of chloride-propylene copolymer and styrene-isoprene copolymer;
(b) said lipophilic-hydrophobic polymer present in said second layer is polyvinyl chloride homopolymer; and
(c) said lipophilic-hydrophobic plasticizer is selected from a first group consisting of nitroarylalkyl ethers, nitroaryl alkylaryl ethers, nitroaryl arylalkyl ethers, bis(nitroaryl)ethers, nitroaryl aryl ethers, dialkyl alkylphosphonates, dialkyl arylphosphonates, diaryl arylphosphonates, diaryl alkylphosphonates, trialkyl phosphates, trialkylaryl phosphates, triaryl phosphates, triarylalkyl phosphates, mixtures thereof and at least one of the above in admixture with at least one compound selected from a group consisting of dialkyl adipates, dialkylaryl adipates, diaryl adipates, and diarylalkyl adipates, wherein each alkyl group contains from 8 to 14 carbon atoms and each aryl group contains 6, 10, or 12 carbon atoms.

52. The electrode of claim 51 wherein said first layer comprises from about 10 to about 60 weight percent of said adhesive lipophilic-hydrophobic polymer ad from about 40 to about 90 weight percent of said lipophilic-hydrophobic plasticizer; and said second layer comprises from about 25 to about 60 weight percent of said polyvinyl chloride homopolymer, from about 30 to about 74.9 weight percent of said lipophilic-hydrophobic plasticizer; and from about 0.1 to about 10 weight percent of said calcium ion selective component.

53. The electrode of claim 52 wherein said first layer comprises from about 15 to about 40 weight percent of said adhesive, lipophilic-hydrophobic polymer and from about 60 to about 85 weight percent of said lipophilic-hydrophobic plasticizer; and said second layer comprises from about 35 to about 45 weight percent of said polyvinyl chloride homopolymer, from about 55 to about 65 weight percent of said lipophilic-hydrophobic plasticizer, and from about 2 to about 6 weight percent of said calcium ion selective component.

54. The electrode of claim 53 wherein said first layer comprises from about 15 to about 25 weight percent of said adhesive, lipophilic-hydrophobic polymer and from about 75 to about 85 weight percent of said lipophilic-hydrophobic plasticizer; and said second layer comprises about 42.5 weight percent of said polyvinyl chloride homopolymer, about 55 weight percent of said lipophilic-hydrophobic plasticizer, and about 2.5 weight percent of said calcium ion selective component.

55. The electrode of claim 54 wherein said adhesive lipophilic-hydrophobic polymer in said first layer has an intrinsic viscosity of from about 0.5 to about 0.7 ml/g, wherein each of said alkyl groups cotains from 8 to 12 carbon atoms; and wherein said polyvinyl chloride homopolymer has an intrinsic viscosity of from about 1 to about 1.3 ml/g.

56. The electrode of claim 55 wherein said adhesive, lipophilic-hydrophobic polymer in said first layer has an intrinsic viscosity of from about 0.6 ml/g; wheren said lipophilic-hydrophobic plasticizer in said first an second layer is the same; and wherein said polyvinyl chloride homopolymer has an intrinsic viscosity of from about 1.1 to about 1.2 ml/g.

57. The electrode of claim 56 wherein said lipophilic-hydrophobic plasticizer is dioctyl phenylphosphonate.

58. The electrode of claims 50–56 or 57 wherein X and Y are the same and are selected from the group consisting of (t-butyl)phenyl, p-(t-butyl)diphenyl, (t-butyl)naphthyl, (n-octyl)phenyl, (iso-octyl)phenyl, (t-octyl)phenyl, (t-octyl)naphthyl, (methyl)phenyl, (ethyl)phenyl, (n-propyl)phenyl, (iso-propyl)phenyl, (n-butyl)-phenyl, (iso-butyl)phenyl, (n-pentyl)phenyl, (n-hexyl)phenyl, (1,2-dimethylbutyl)phenyl, (2-ethylhexyl)phenyl, (isononyl)phenyl, (n-decyl)phenyl, (iso-decyl)phenyl, and (n-dodecyl)phenyl; and wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl.

59. The electrode of claims 50–56 or 57 wherein X and Y are the same and are selected from a group consisting of p-(1,1,3,3-tetramethylbutyl)phenyl, p-(iso-decyl)phenyl, p-(n-decyl)phenyl, p-(2-ethylhexyl)phenyl, and p-(n-octyl)phenyl; and wherein Z is ethyl.

60. The electrode of claims 50–56 or 57 wherein X and Y are the same and are selected from the group consisting of cyclohexyl, cyclooctyl, cyclooctenyl, octenyl-1, cyclododecyl, dodecenyl-1, t-butyl, 3-butenyl, n-octyl, iso-octyl, t-octyl, methyl, ethyl, -propyl, iso-propyl, n-butyl, iso-butyl, n-pentyl, n-hexyl, 2,3- dimethylbutyl, 2-ethylhexyl, iso-nonyl, n-decyl, iso-decl, and n-dodecyl; and wherein Z is selected from a group consisting of cyclohexyl, cyclooctyl, cyclooctenyl, octenyl-1, cyclododecyl, dodecenyl-1, t-butyl, -octyl, t-octyl, methyl, ethyl, n-propyl, iso-propyl, n-butyl, 3-butenyl, sec-butyl, n-pentyl, n-nexyl, 1-heptynyl, 1,2-dimethylbutyl, 2-ethylhexyl, n-decyl, and n-dodecyl.

61. The electrode of claims 50–56 or 57 wherein X and Y are the same and are selected from the group consisting of n-octyl, iso-nonyl, n-dodecyl, oleyl, n-decyl, and iso-decyl; and wherein Z is ethyl.

62. The electrode of claim 42 wherein said membrane comprises:
   (a) a first lipophilic-hydrophobic layer comprising:
      (i) an adhesive, lipophilic-hydrophobic polymer having an intrinsic viscosity of from about 0.2 to about 0.9 ml/g;
      (ii) a lipophilic-hydrophobic plasticizer; and
      (iii) said calcium ion-selective component; and
   (c) a second lipophilic-hydrophobic layer in intimate contact with said first layer, said second layer comprising:
      (i) a lipophilic-hydrophobic polymer having an intrinsic viscosity of from about 1 to about 1.5 ml/g;
      (ii) a lipophilic-hydrophobic plasticizer; and
      (iii) said calcium ion-selective component.

63. The electrode of claim 62 wherein:
   (a) said adhesive, lipophilic-hydrophobic polymer present in said first layer is selected from a group consisting of chloride-propylene copolymer and styrene-isoprene copolymer;
   (b) said lipophilic-hydrophobic polymer present in said second layer is polyvinyl chloride homopolymer; and
   (c) said lipophilic-hydrophobic plasticizer is selected from a first group consisting of nitroaryl alkyl ethers, nitroaryl alkylaryl ethers, nitroaryl arylalkyl ethers, bis(nitroaryl)ethers, nitroaryl aryl ethers, dialkyl alkylphosphonates, dialkyl arylphosphonates, diaryl arylphosphonates, diaryl alkylphosphonates, trialkyl phosphates, trialkylaryl phosphates, triaryl phosphates, triarylalkyl phosphates, mixtures thereof and at least one of the above in admixture with at least one compound selected from a group consisting of dialkyl adipates, dialkylaryl adipates, diaryl adipates, and diarylalkyl adipates, wherein each alkyl group contains from about 8 to about 14 carbon atoms and each aryl group contains 6, 10, or 12 carbon atoms.

64. The electrode of claim 63 wherein said first layer comprises from about 10 to about 60 weight percent of said adhesive lipophilic-hydrophobic polymer, from about 35 to about 89.99 weight percent of said lipophilic-hydrophobic plasticizer, and from about 0.01 to about 5 weight percent of said calcium selective component; and said second layer comprises from about 25 to about 60 weight percent of said polyvinyl chloride homopolymer, from about 30 to about 74.9 weight percent of said lipophilic-hydrophobic plasticizer; and from about 0.1 to about 10 weight percent of said calcium selective component.

65. The electrode of claim 64 wherein said first layer comprises from about 12.5 to about 40 weight percent of said adhesive, lipophilic-hydrophobic polymer, from about 59 to about 87 weight percent of said lipophilic-hydrophobic plasticizer, and from about 0.05 to about 1 weight percent of said calcium selective component; and said second layer comprises from about 35 to about 45 weight percent of said polyvinyl chloride homopolymer, from about 55 to about 65 weight percent of said lipophilic-hydrophobic plasticizer, and from about 2 to about 6 weight percent of said calcium selective component.

66. The electrode of claim 65 wherein said first layer comprises from about 14.9 to about 25 weight percent of said adhesive, lipophilic-hydrophobic polymer, from about 74.5 to about 85 weight percent of said lipophilic-hydrophobic plasticizer, and from about 1 to about 0.5 weight percent of said calcium selective component; and said second layer comprises about 42.5 weight percent of said polyvinyl chloride homopolymer, about 55 weight percent of said lipophilic-hydrophobic plasticizer, and about 2.5 weight percent of said calcium selective component.

67. The electrode of claim 66 wherein said adhesive, lipophilic-hydrophobic polymer in said first layer has an intrinsic viscosity of from about 0.5 to about 0.7 ml/g and wherein said lipophilic-hydrophobic polymer in said second layer has an intrinsic viscosity of from about 1 to about 1.3 ml/g.

68. The electrode of claim 67 wherein said adhesive, lipophilic-hydrophobic polymer in said first layer has an intrinsic viscosity of about 0.6 ml/g and wherein said lipophilic-hydrophobic polymer in said second layer has an intrinsic viscosity of about 1.1 to about 1.2 ml/g.

69. The electrode of claim 68 wherein said adhesive lipophilic-hydrophobic polymer in said first layer has an intrinsic viscosity of from about 0.5 to about 0.7 ml/g, wherein each of said alkyl groups contains from 8 to 12 carbon atoms; and wherein said polyvinyl chloride homopolymer has an intrinsic viscosity of from about 1.0 to about 1.3 ml/g.

70. The electrode of claim 69 wherein said adhesive, lipophilic-hydrophobic polymer in said first layer has an intrinsic viscosity of about 0.6 ml/g; wherein said lipophilic-hydrophobic plasticizer in said first and second layer is the same; and wherein said polyvinyl chloride homopolymer has an intrinsic viscosity of from about 1.1 to about 1.2 ml/g.

71. The electrode of claim 70 wherein said lipophilic-hydrophobic plasticizer is dioctyl phenylphosphonate.

72. The electrode of claims 62–70 or 71 wherein X and Y are the same and are selected from the group consisting of (t-butyl)phenyl, p-(t-butyl)diphenyl, (t-butyl)naphthyl, (n-octyl)phenyl, (iso-octyl)phenyl, (t-octyl)phenyl, (t-octyl)naphthyl, (methyl)phenyl, (ethyl)phenyl, (n-propyl)phenyl, (iso-propyl)phenyl, (n-butyl)phenyl, (iso-butyl)phenyl, (n-pentyl)phenyl, (n-hexyl)phenyl, (1,2-dimethylbutyl)phenyl, (2-ethylhexyl)phenyl, (iso-nonyl)phenyl, (n-decyl)phenyl, (iso-decyl)phenyl, and (n-dodecyl)phenyl; and wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, se-butyl, n-pentyl, n-hexyl, 1-heptynyl, 1,2-dimethylbutyl, 2-ethylhexyl, n-decyl, and n-dodecyl.

73. The electrode of claims 62–70 or 71 wherein X and Y are the same and are selected from a group consisting of p-(1,1,3,3-tetramethylbutyl)phenyl, p-(iso-decyl)phenyl, p-(n-decyl)phenyl, p-(2-ethylhexyl)phenyl, and p-(n-octyl)phenyl; and wherein Z is ethyl.

74. The electrode of claims 62–70 or 71 wherein X and Y are the same and are selected from the group consisting of cyclohexyl, cyclooctyl, cyclooctenyl, octenyl-1, cyclododecyl, dodecenyl-1, t-butyl, 3-butenyl, n-octyl, iso-octyl, t-octyl, methyl, ethyl, n-propyl, iso-propyl, n-butyl, iso-butyl, n-pentyl, n-hexyl, 1,2-dimethylbutyl, 2-ethylhexyl, iso-nonyl, n-decyl, iso-decyl, and n-dodecyl; and wherein Z is selected from a group consisting of cyclohexyl, cyclooctyl, cyclooctenyl, octenyl-1, cyclododecyl, dodecenyl-1, t-butyl, n-octyl, t-octyl, methyl, ethyl, n-propyl, iso-propyl, n-butyl, 3-butenyl, sec-butyl, n-pentyl, n-hexyl, 1-heptynyl, 1,2-dimethylbutyl, 2-ethylhexyl, n-decyl, and n-dodecyl.

75. The electrode of claims 62–70 or 71 wherein X and Y are the same and are selected from the group consisting of n-octyl, iso-nonyl, n-dodecyl, oleyl, n-decyl, and iso-decyl; and wherein Z is ethyl.

* * * * *